(12) United States Patent
Baumgartner

(10) Patent No.: US 8,970,207 B2
(45) Date of Patent: Mar. 3, 2015

(54) DEVICE FOR MEASURING DRILL BIT DISPLACEMENT

(75) Inventor: Adrian Baumgartner, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 294 days.

(21) Appl. No.: 13/472,926

(22) Filed: May 16, 2012

(65) Prior Publication Data
US 2013/0307529 A1  Nov. 21, 2013

(51) Int. Cl.
G01B 7/14 (2006.01)

(52) U.S. Cl.
USPC .................................. 324/207.2; 324/207.24

(58) Field of Classification Search
USPC .......................................... 324/207.24, 207.2
See application file for complete search history.

(56) References Cited

U.S. PATENT DOCUMENTS

| | | | |
|---|---|---|---|
| 3,133,457 A * | 5/1964 | Martens | 408/6 |
| 3,747,085 A * | 7/1973 | Bala et al. | 340/680 |
| 5,450,009 A * | 9/1995 | Murakami | 324/207.21 |
| 2005/0116673 A1 | 6/2005 | Carl et al. | |
| 2007/0035311 A1 | 2/2007 | Wuersch | |
| 2009/0326537 A1 * | 12/2009 | Anderson | 606/80 |
| 2010/0137874 A1 | 6/2010 | Kim et al. | |
| 2010/0206671 A1 | 8/2010 | Cahill | |
| 2010/0274121 A1 | 10/2010 | Ritchey et al. | |
| 2011/0245833 A1 * | 10/2011 | Anderson | 606/80 |

FOREIGN PATENT DOCUMENTS

WO   WO 2009/158115   12/2009

OTHER PUBLICATIONS

International Patent Application No. PCT/US2013/040086: Partial International Search Report.

* cited by examiner

*Primary Examiner* — Jay Patidar
(74) *Attorney, Agent, or Firm* — Baker & Hostetler LLP

(57) ABSTRACT

A measuring device 1 configured to receive a drill bit 3, and determine the relative displacement of the drill bit 3, is disclosed. The measuring device 1 is configured to be deployed proximate to the material to be drilled, reset, and subsequently determine the relative displacement of the drill bit 3. The measuring device 1 can be used in orthopaedic surgery procedures for determining the depth of a bore hole in bone.

27 Claims, 6 Drawing Sheets

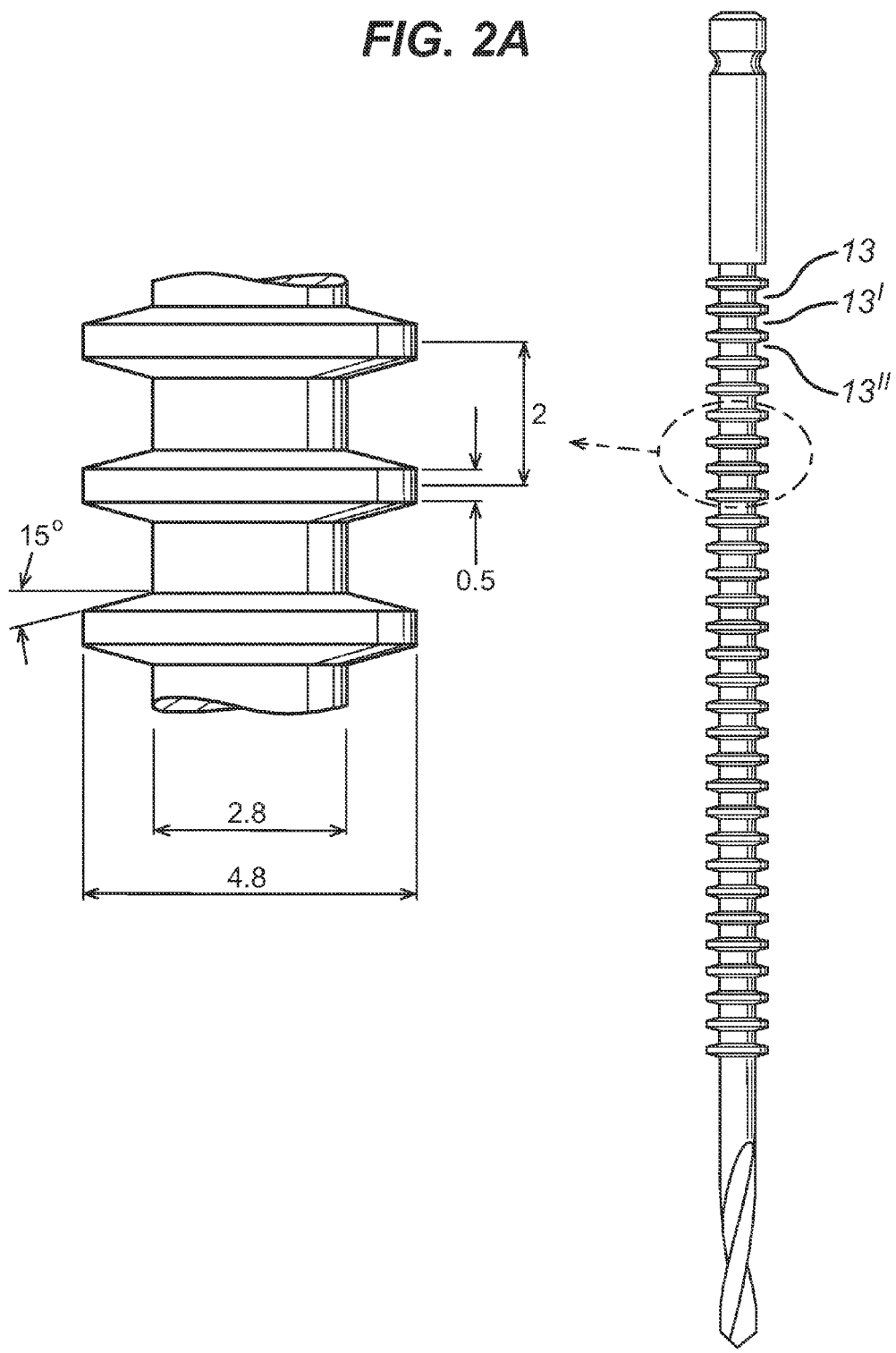

FIG. 3
FIG. 4
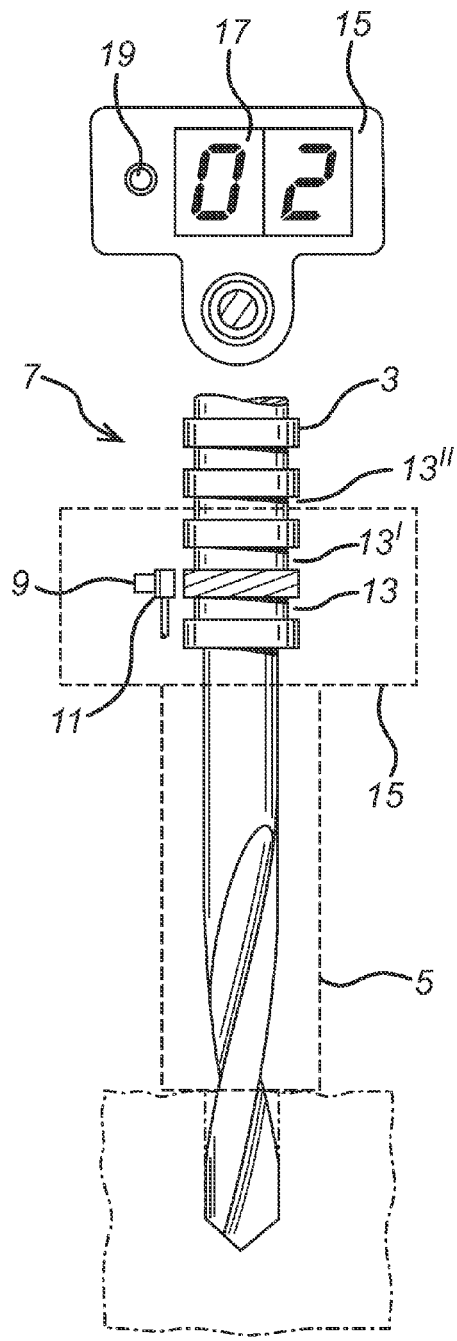
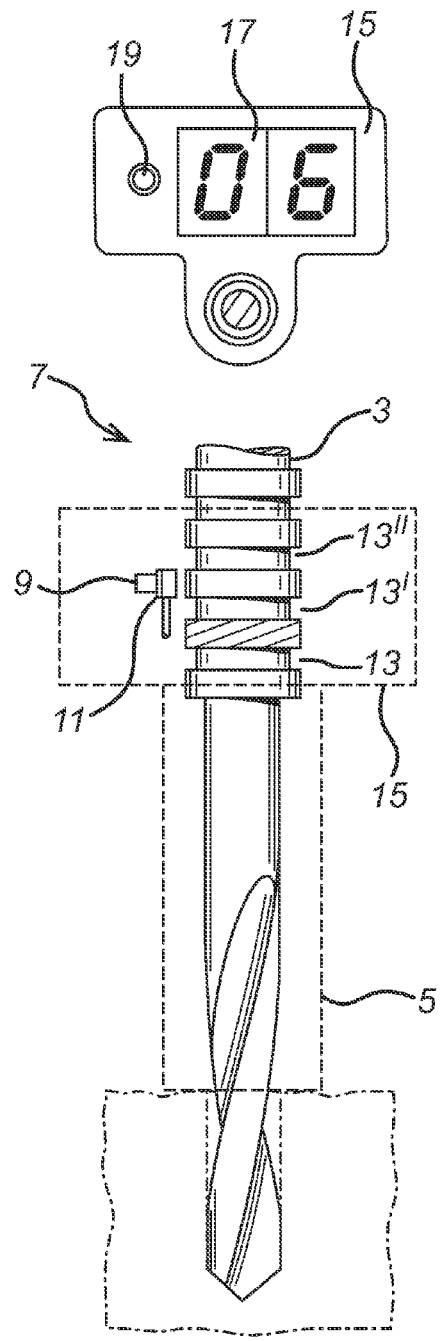

DEVICE FOR MEASURING DRILL BIT DISPLACEMENT

FIELD OF THE DISCLOSURE

The present invention relates to measuring devices, and in particular, a device for measuring the depth of a bore hole in bone.

BACKGROUND

In certain orthopaedic surgery procedures, a surgeon will have to drill holes in bone to subsequently accommodate a screw type. It is therefore essential to the procedure at hand that the depth of a bore hole in bone that has been drilled is accurately determined so that the appropriate screw type can be selected.

A common know procedure is to measure the depth of the bore hole using a standard mechanical/electronic depth gauge after drilling. However, this can lead to incorrect depths being obtained as the depth is only determined after the drilling has been completed. In addition, it can require several drilling steps to obtain the desired depth. Such a prior art device is known from US2010/0137874A1.

Another known option is to use drills with a scale and slider to indicate drill depth. However, obtaining an accurate reading from the scale can be a cumbersome process, especially when operating the drill. The problem is exaggerated when using small diameter drill bits.

SUMMARY

In a first aspect, there is provided a measuring device for a drill comprising a sensor configured to receive a drill bit and determine the relative displacement of the drill bit. This may allow the depth of the drill bit within a bore hole to be easily and accurately determined, either during or after the drilling process.

The sensor can have a conduit for receiving the drill bit. This may allow the relative displacement of the drill bit to be determined. The sensor may use an incremental encoder for accurately determining the displacement. The incremental encoder can be triggered by the drill bit interacting with either a mechanical, magnetic or electromagnetic sensor. A hall sensor or a sensor using an electromagnetic field generating component may be used for this purpose.

The sensor may advantageously be adapted to interact with a repetitive feature of the drill bit. This ensures accuracy in determining the relative displacement of drill bit. The repetitive feature may include grooves. The grooves may be filled with a plastics material, creating a flush outer surface for the drill bit, which aids sterilisation of the drill bit. A plastics material such as PEEK (Polyether ether ketone) may be appropriate.

Alternatively, the device sensor can be adapted to interact with a multi-pole magnetic sleeve for placement over a drill bit. This allows the use of standard drill bit.

Alternatively, the device sensor may be adapted to interact with a magnetic coating of drill bit. The magnetic coating may have a predetermined coded sequence of magnetic poles. This allows the use of standard drill bit. This coating may be applied to a standard drill bit.

The measuring device may comprise a housing that is integral with the sensor. The housing can display the relative displacement of the drill bit. This provides the user with a clear indication of the depth of the bore hole. Alternatively, the housing may be disposed remotely to the sensor and communicate wirelessly therewith, providing the user with an unobstructed view of the display.

The display may take the form of a touch screen for facilitating user interaction. The display may also advantageously indicate a screw/implant type required based on the relative displacement of the drill bit. The housing can also comprise a reset button for setting up the device prior to taking a measurement. The housing can also comprise a suitable power source and control circuitry.

The display may provide a menu based interface to facilitate user interaction, which can be advantageously navigated using at least one of a button, a trackball, or a thumb-joystick.

Embodiments in accordance with other aspects of the present invention comprise a drill bit or drill configured for use with the measuring device.

The present invention further provides a method of determining the relative displacement of a drill bit using a measuring device, comprising receiving a drill bit within a sensor, sensing motion of the drill bit through the sensor, and determining the relative displacement of the drill bit.

BRIEF DESCRIPTION OF THE DRAWINGS

The present invention will now be described in detail with reference to the accompanying drawings, in which:

FIGS. 2 & 2a show a drill bit in accordance with the present invention;

FIGS. 3 & 4 show how a sensor in accordance with the present invention is implemented;

DETAILED DESCRIPTION

Figure 1:
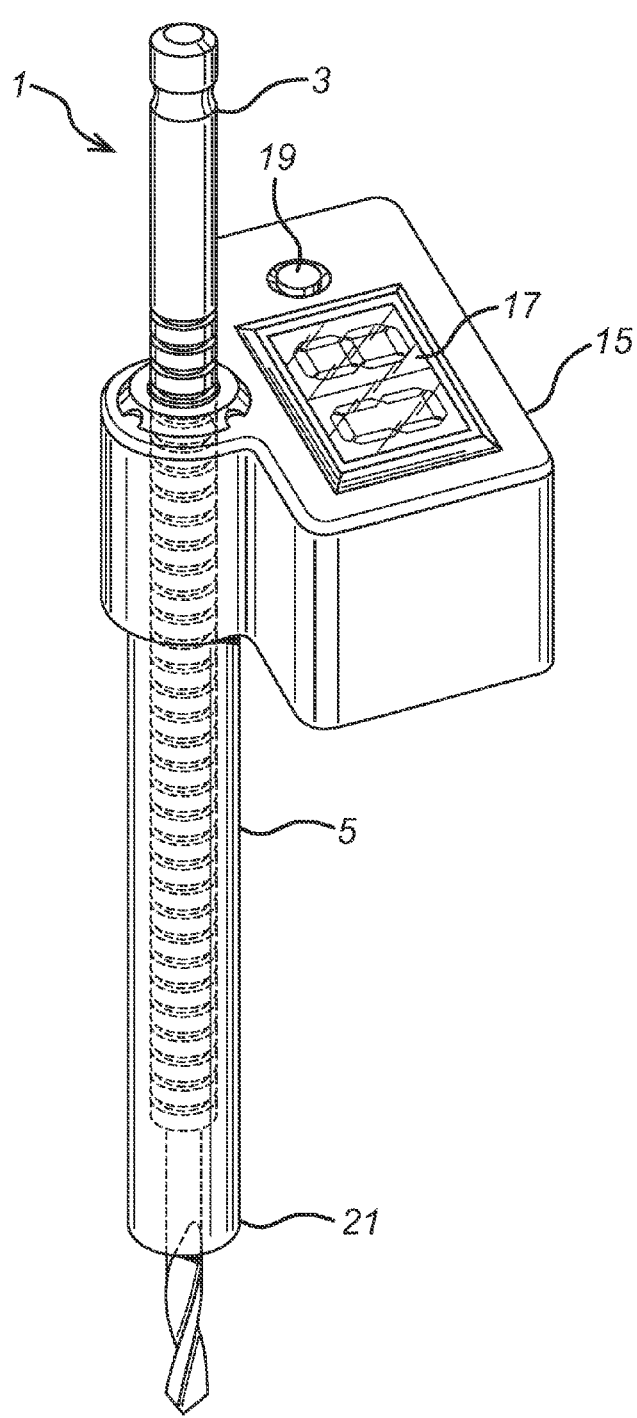
FIG. 1 shows a perspective view of a measuring device in accordance with the present invention.

In the drawings, a measuring device 1 is configured to receive a drill bit 3, and determine the relative displacement of the drill bit 3. The measuring device comprises a conduit 5 for receiving and guiding the drill bit 3. The length and diameter of the conduit 5 can be configured to accommodate drill bits having diameters that fall within a specific range. Alternatively, the conduit can be configured to accommodate a specific drill bit.

The measuring device 1 further comprises an incremental encoder 7 for measuring the relative displacement of the drill bit 3. The incremental encoder can be triggered by the drill bit interacting with either a mechanical, magnetic or electromagnetic sensor. In the illustrated embodiment, a hall sensor 11 (see FIG. 3) detects the change in magnetic field as the drill bit 3 moves relative to the hall sensor 11. The hall sensor also incorporates a magnet 9. A cyclic change in magnetic field can be used to establish the relative displacement of the drill bit 3 as it moves through the conduit 5. In an alternate embodiment a differential transformer sensor is used instead of the hall sensor 11. An example of such a sensor is a "Sensor ID1101G" produced by POSIC, which is currently designed to be used for gear wheel tooth detection.

Figure 2:
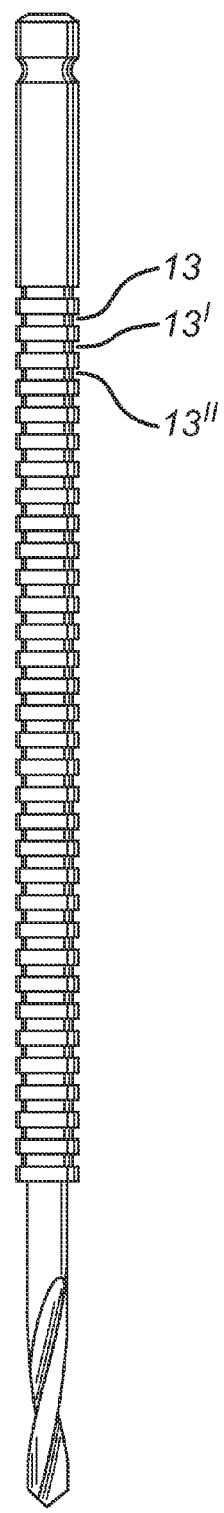

In accordance with the present invention, the cyclic change in magnetic field that is indicative of relative displacement can be generated by a repetitive feature of the drill bit 3. The repetitive feature can take the form of circumferential grooves 13, 13', 13" disposed along the length of the drill bit 3. The grooves may be truncated as shown in FIG. 2A. FIG. 2A also indicates the dimensions in mm, and pitch angle of the truncated grooves in a preferred embodiment of the present invention. Although shown as regularly spaced grooves 13, 13', 13", the grooves 13, 13', 13" may be disposed irregularly. The spacing of the grooves 13, 13', 13" can be set depending on the tolerance required for the procedure at hand. Additionally, the grooves may be filled with a plastics material, which is preferably non-magnetic. An example plastics material is PEEK (Polyether ether ketone). This allows the drill bit 3 to maintain a flush outer surface, which aids sterilization.

Figure 5:
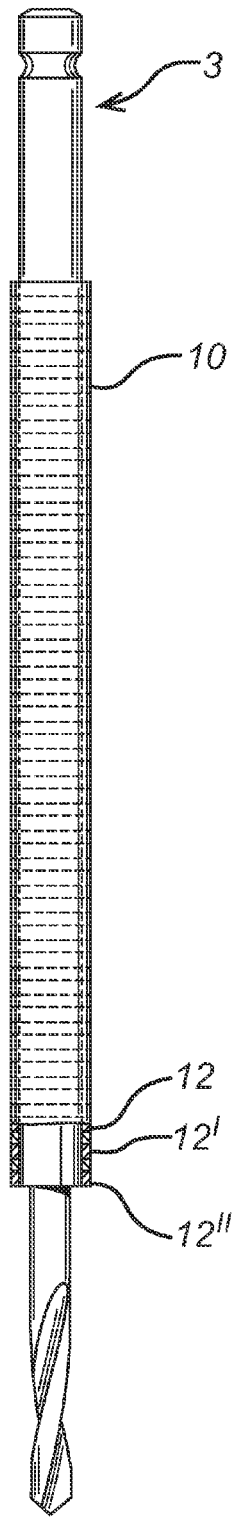
FIG. 5 shows a sleeve for use with a drill bit in accordance with the present invention.

The underlying principle of detecting a cyclic change in magnetic field that is indicative of relative displacement can be applied by other means. Other means in the form of magnetic sensors includes a magneto-transistor, a magnetoresistance sensor, an AMR magnetometer, a MEMS sensor, a MEMS compass, a fluxgate magnetometer or a search coil magnetic field sensor. Other means include the use of an electromagnetic field generating component with a hall sensor that is triggered by a repetitive feature of the drill bit 3. Alternatively, a mechanical sensor can be adapted to be triggered by the grooves 13, 13', 13". Alternatively, as shown in FIG. 5, a sleeve 10 for receiving a drill bit 3 may be used to implement the incremental encoder 7. Magnetic poles 12, 12' 12" on the sleeve can trigger a sensor (not depicted), such as a reed switch, thereby providing a cyclic indication used to establish the relative displacement of the drill bit 3 as it moves through the conduit 5. The magnetic poles 12, 12' 12" may be disposed either regularly or irregularly depending on the measuring device setup. The spacing of the magnetic poles 12, 12' 12"can also be set depending on the tolerance required for the procedure at hand.

Figure 6:
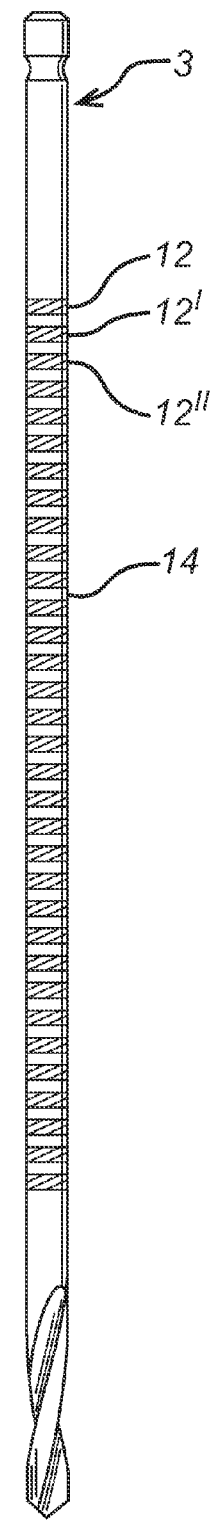
FIG. 6 shows a drill bit with a magnetic coating in accordance with the present invention.
Figure 7:
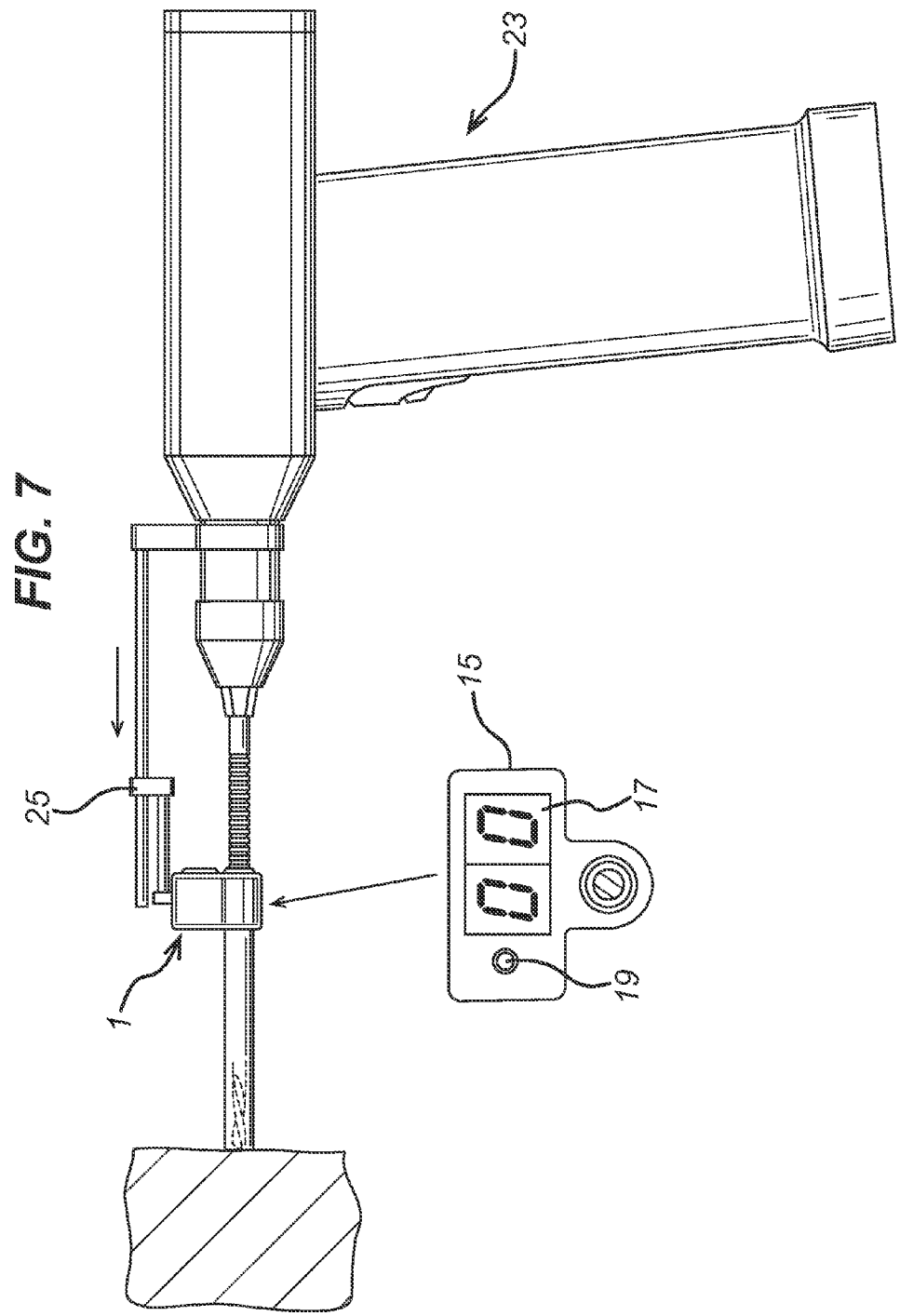
FIGS. 7 & 8 show a drill in accordance with the present invention.
Figure 8:
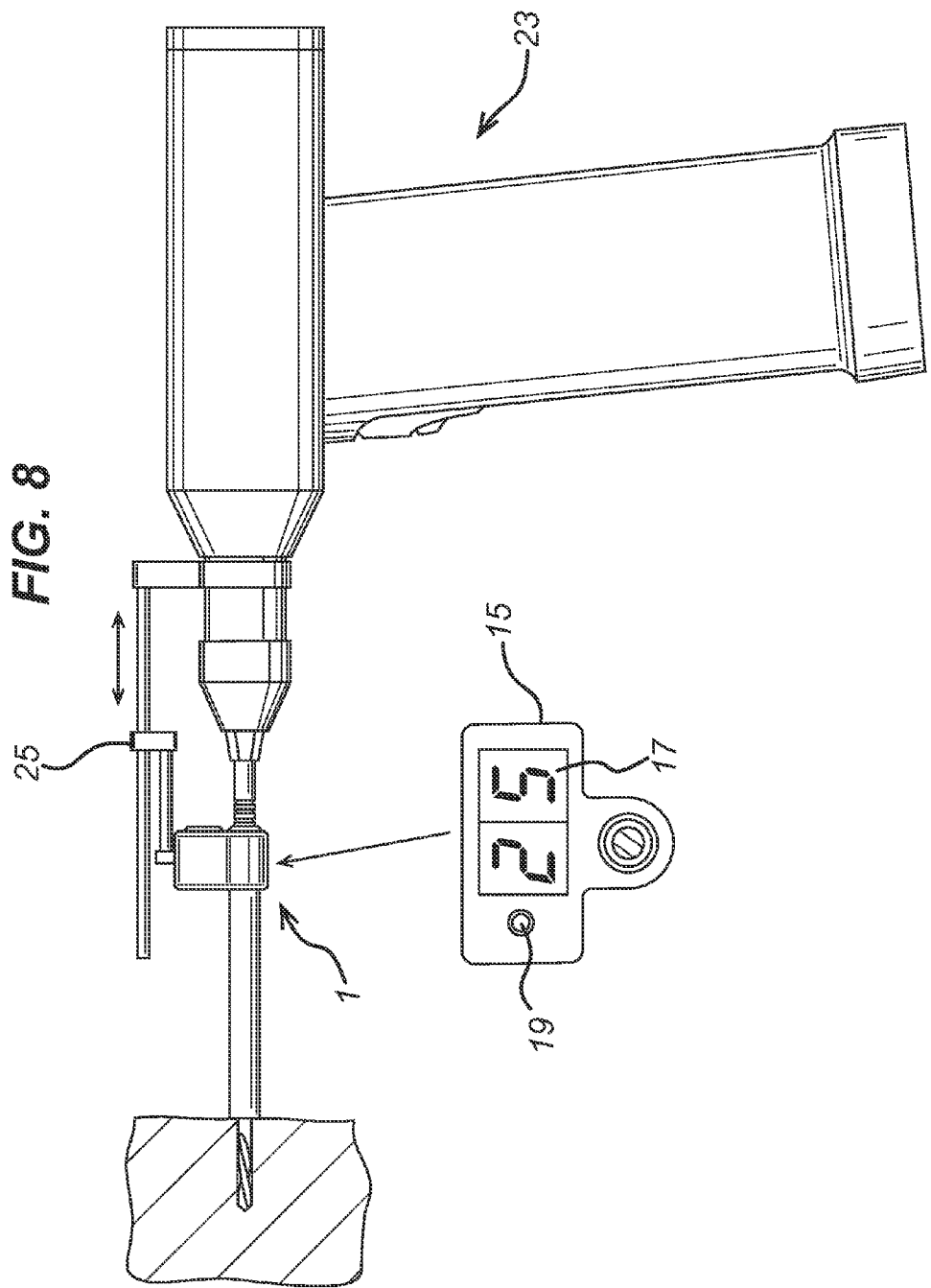

As an alternative to using a sleeve 10, a drill bit 3 shown in FIG. 6 may be provided with a magnetic coating 14 having predefined magnetic poles.

The measuring device further comprises a housing 15. Although the housing 15 is depicted as integral with the conduit 5, it may be remotely located and communicate wirelessly with the incremental encoder 7. The housing contains a display 17 for indicating the relative displacement of the drill bit 3. The display 17 may take the form of an LCD or LED display, such as a seven segment display.

A reset button 19 allows the measurement to be reset to zero. The display will receive an output from the incremental encoder 7 and indicate the relative movement of the drill bit 3 from the position it was at when the reset button 19 was pressed. This allows the measuring device 1 to adopt a wide range of positions relative to the drill bit prior to commencing drilling and/or measurement. This can also be particularly useful if a drilling process is used in which bores of different diameters are drilled sequentially.

The display 17 may optionally comprise touch screen functionality integrated with a menu based user interface (not depicted). In addition, this user interface can be navigated using at least one of a button, a trackball, or thumb joystick (not depicted). The display can further indicate to the user a screw/implant type required based on the measured relative displacement of the drill bit (and hence hole drilled). The user can optionally configure the device to apply an offset to the measured relative displacement when indicating a screw/implant type required. The user can also indicate the type of drill bit 3 that is to be used for drilling, so that the incremental encoder can be calibrated accordingly.

The housing 15 also contains control circuitry and a power source. The power source may be controlled by the reset button 19.

An exemplary method of using the device will now be described. The measuring device is placed with an end 21 of the conduit flush against the material (e.g. bone cortex) to be drilled. A drill bit 3 is received within the conduit. The reset button 19 of the device is pressed to 'zero' the device. The drilling operation commences. The movement of the drill bit 3 with circumferential grooves 13, 13', 13" (disposed substantially parallel to one another and substantially perpendicular to the length of the drill bit) past the hall sensor 9 (which is placed next to the drill bit at a distance of approximately 0.6 mm) creates a cyclic change in magnetic field. The number of recurrences of the cyclic change is indicative of the relative displacement of the drill bit 3, and is displayed on the display 17. Thereafter, an appropriate screw/implant type may be indicated on the display.

Although the device can be used separately from a drill in a freehand manner, as may be the case in confined areas which do not permit access by anything other than the drill bit, the device can be easily adapted to connect integrally with a drill 23. A mounting device 25 allows the drill bit to move relative to the measuring device 1. This ensures an accurate displacement reading from the measurement device 1. The measuring device 1 can also be used with various guide instruments that are well known in the art, such as an aiming arm.

It will be appreciated that this description is by way of example only; alterations and modifications may be made to the described embodiment without departing from the scope of the invention as defined in the claims.

The invention claimed is:

1. A measuring device configured to measure a depth of a bore hole in bone, the measuring device comprising:
    a housing defining a bore along an axial direction, the bore sized and configured to receive a drill bit; and
    a sensor supported by the housing and positioned along a path that extends in a radial direction, perpendicular to the axial direction, from a central axis of the bore such that the sensor is aligned with the bore along the radial direction,
    wherein the sensor is configured to sense, when the drill bit extends through the bore, displacement of the drill bit within the bore as the drill bit is creating the bore hole in the bone.

2. The measuring device according to claim 1, further comprising a conduit attached to the housing for receiving the drill bit.

3. The measuring device according to claim 1, wherein the sensor is a magnetic sensor configured to sense movement of the drill bit.

4. The measuring device according to claim 3, wherein the sensor comprises a hall sensor.

5. The measuring device according to claim 4, wherein the sensor comprises a magnetic field generating component.

6. The measuring device according to claim 1, wherein the sensor is an electromagnetic sensor configured to sense movement of the drill bit.

7. The measuring device according to claim 6, wherein the sensor comprises an electromagnetic field generating component.

8. The measuring device according to claim 1, wherein the sensor is configured to detect a repetitive feature of the drill bit.

9. The measuring device according to claim 8, wherein the repetitive feature comprises circumferential grooves formed in the drill bit, the circumferential grooves spaced apart along the axial direction between the opposed first and second ends of the drill bit.

10. The measuring device according to claim 1, wherein the device further comprises a multi-pole magnetic sleeve for placement over a drill bit.

11. The measuring device according to claim 1, wherein the housing comprises a display.

12. The measuring device according to claim 11, wherein the display indicates the relative displacement of the drill bit.

13. The measuring device according to claim 12, wherein the display indicates at least one of a screw type and an implant type required based on the relative displacement of the drill bit.

14. The measuring device according to claim 1, wherein the housing comprises a reset button configured to reset the sensed displacement to zero.

15. The measuring device of claim 1, wherein the sensor is configured to sense movement of the drill bit past the sensor in the axial direction.

16. The measuring device of claim 1, wherein the sensor is configured to detect a cyclic change in a magnetic field, the cyclic change indicative of the displacement of the drill bit.

17. The measuring device of claim 1, wherein the bore extends entirely through the housing.

18. A method of measuring a depth of a bore hole in bone using a measuring device, the method comprising:
(a) receiving a drill bit within a bore defined in a housing of the measuring device so as to position a sensor supported by the housing along a path that extends radially from a central axis of the drill bit at a location between opposed first and second ends of the drill bit, the opposed first and second ends spaced apart with respect to an axial direction that is perpendicular to the path;
(b) drilling the bore hole into the bone and sensing a displacement of the drill bit relative to the sensor as the drill bit is creating the bore hole; and
(c) determining the depth of the bore hole based on the displacement of the drill bit.

19. The method according to claim 18, comprising:
resetting the sensed displacement to zero after step (a) and before step (b).

20. The method of claim 18, wherein step (b) comprises sensing movement of the drill bit past the sensor in the axial direction.

21. The method of claim 18, wherein step (b) comprises detecting a cyclic change in a magnetic field, the cyclic change indicative of the displacement of the drill bit.

22. A system configured to measure a displacement of a drill bit, the system comprising:
a drill bit;
a housing defining a bore along an axial direction, the bore sized and configured to receive the drill bit; and
a sensor supported by the housing and positioned along a path that extends in a radial direction, perpendicular to the axial direction, from a central axis of the bore such that the sensor is aligned with the bore along the radial direction,
wherein the sensor is configured to sense, when the drill bit extends through the bore, displacement of the drill bit within the bore as the drill bit is creating the bore hole in the bone.

23. The system according to claim 22, wherein:
the drill bit comprises a repetitive structure; and
the sensor is configured to sense displacement of the repetitive structure to determine the depth of the bore hole.

24. The system according to claim 23, wherein the repetitive structure is defined by circumferential grooves formed in the drill bit, the circumferential grooves spaced apart along the axial direction between the opposed first and second ends of the drill bit.

25. The system according to claim 24, wherein the circumferential grooves are parallel and substantially perpendicular to the central axis of the drill bit.

26. The system according to claim 23, wherein the repetitive structure comprises a magnetic coating formed on the drill bit, the magnetic coating having magnetic poles spaced apart along the axial direction between the opposed first and second ends of the drill bit.

27. The system according to claim 22, further comprising a magnetic sleeve configured to receive the drill bit, the magnetic sleeve having magnetic poles spaced apart along the axial direction, wherein the sensor is configured to sense displacement of the magnetic poles relative to the sensor to determine the depth of the bore hole.

* * * * *